(12) United States Patent
Lin

(10) Patent No.: US 11,052,216 B2
(45) Date of Patent: *Jul. 6, 2021

(54) ANTI-EXPLOSION GAS GENERATOR FOR HEALTH USE

(71) Applicant: Hsin-Yung Lin, Shanghai (CN)

(72) Inventor: Hsin-Yung Lin, Shanghai (CN)

( * ) Notice: Subject to any disclaimer, the term of this patent is extended or adjusted under 35 U.S.C. 154(b) by 261 days.

This patent is subject to a terminal disclaimer.

(21) Appl. No.: 16/219,267

(22) Filed: Dec. 13, 2018

(65) Prior Publication Data

US 2019/0186028 A1 Jun. 20, 2019

Related U.S. Application Data

(63) Continuation of application No. 14/227,703, filed on Mar. 27, 2014, now Pat. No. 10,190,224.

(30) Foreign Application Priority Data

Jun. 19, 2013 (CN) .......................... 201320352900.3

(51) Int. Cl.
*A61M 16/12* (2006.01)
*A61M 16/14* (2006.01)
(Continued)

(52) U.S. Cl.
CPC ........ *A61M 16/14* (2013.01); *A61M 16/0051* (2013.01); *A61M 16/021* (2017.08);
(Continued)

(58) Field of Classification Search
CPC .............. A61M 16/00; A61M 16/0003; A61M 16/0051; A61M 16/0087; A61M 16/021;
(Continued)

(56) References Cited

U.S. PATENT DOCUMENTS

| 5,672,581 A | 9/1997 | Rubsamen | |
|---|---|---|---|
| 2002/0185126 A1* | 12/2002 | Krebs | .................. A61M 16/12 128/200.24 |

(Continued)

FOREIGN PATENT DOCUMENTS

CN 202576577 12/2012

OTHER PUBLICATIONS

Ono H, et al. "A basic study on molecular hydrogen (H2) inhalation in acute cerebral ischemia patients for safety check with physiological parameters and measurement of blood H2 level." Med Gas Res. Aug. 23, 2012;2(1):21. doi: 10.1186/2045-9912-2-21.*

(Continued)

*Primary Examiner* — Joseph D. Boecker

(57) ABSTRACT

An anti-explosion gas generator for health use is provided. The anti-explosion gas generator for health use includes an electrolysis device for electrolyzing water to produce a gas mixture of hydrogen and oxygen. The gas generator for health use further includes a gas mixing system coupled to the electrolysis device for receiving the gas mixture. The gas mixing system mixes the gas mixture with water vapor, an atomized medicine, a volatile essential oil or a combination thereof to produce a health gas. The health gas is provided for being inhaled by a user.

3 Claims, 2 Drawing Sheets

(51) Int. Cl.
*A61M 16/16* (2006.01)
*C25B 1/04* (2021.01)
*A61M 16/00* (2006.01)
*C25B 15/08* (2006.01)
*C25B 9/00* (2021.01)
*C25B 9/17* (2021.01)
*A61M 21/02* (2006.01)
*A61M 16/10* (2006.01)
*A61M 15/08* (2006.01)
*A61M 21/00* (2006.01)

(52) U.S. Cl.
CPC .......... *A61M 16/12* (2013.01); *A61M 16/122* (2014.02); *A61M 16/125* (2014.02); *A61M 16/16* (2013.01); *A61M 21/02* (2013.01); *C25B 1/04* (2013.01); *C25B 9/00* (2013.01); *C25B 9/17* (2021.01); *C25B 15/08* (2013.01); *A61M 15/08* (2013.01); *A61M 16/107* (2014.02); *A61M 2021/0016* (2013.01); *A61M 2202/0208* (2013.01); *A61M 2205/8231* (2013.01); *Y02E 60/36* (2013.01)

(58) Field of Classification Search
CPC ................ A61M 16/022; A61M 16/10; A61M 16/1005; A61M 16/12; A61M 16/122; A61M 16/125; A61M 16/14; A61M 16/16; A61M 2016/0027; A61M 2016/0033; A61M 2016/0039; A61M 2016/102; A61M 21/02; A61M 2202/02; A61M 2202/0208; A61M 2205/8256; C25B 1/04; C25B 9/06; C25B 15/08; Y02E 60/36; Y02E 60/366
See application file for complete search history.

(56) References Cited

U.S. PATENT DOCUMENTS

| | | | |
|---|---|---|---|
| 2003/0136402 A1 | 7/2003 | Jiang | |
| 2009/0014901 A1 | 1/2009 | Spiegelman | |
| 2010/0089395 A1 | 4/2010 | Power et al. | |
| 2013/0112550 A1 | 5/2013 | Marsh et al. | |
| 2013/0168234 A1* | 7/2013 | Lin | F24F 6/02 204/228.2 |
| 2013/0168235 A1* | 7/2013 | Lin | A61L 9/122 204/228.2 |
| 2013/0206586 A1* | 8/2013 | Lin | C25B 9/06 204/228.2 |
| 2015/0190604 A1* | 7/2015 | Lin | A61M 16/16 128/202.26 |

OTHER PUBLICATIONS

Ohsawa I, et al. "Hydrogen acts as a therapeutic antioxidant by selectively reducing cytotoxic oxygen radicals." Nat Med. Jun. 2007; 13(6):688-94. doi: 10.1038/nm1577.*

* cited by examiner

ANTI-EXPLOSION GAS GENERATOR FOR HEALTH USE

CROSS-REFERENCE TO RELATED APPLICATIONS

This application is a continuation of U.S. application Ser. No. 14/227,703, filed Mar. 27, 2014 which claims the priority benefit of Chinese Application Serial No. 201310244278.9 filed Jun. 19, 2013 the disclosure of which is incorporated herein by reference.

BACKGROUND OF THE INVENTION

1. Field of the Invention

The present invention relates to a gas generator for health use, more particularly, a anti-explosion gas generator for health use that can produce a combination gas of hydrogen and oxygen.

2. Description of the Prior Art

From ancient times till now, humanity has always made preserving life a high priority. Many developments in medical technology are used for diseases and increasing life expectancy. In the past, most medical treatment was passive. In other words, diseases are treated only when people fall ill, by performing surgical operation, medication, chemotherapy, radiation treatment and so on. But recently, many medical experts are focusing on disease prevention, such as studying on the health effects of food, and screening for genetic disorders to actively reduce the risk of falling ill. Furthermore, to increase life expectancy, many anti-aging technologies have been developed, including skin care products and antioxidant food/medicine.

In recent years, people have been noticing the benefits of aromatherapy. Aromatherapy is a natural way to make people feel relaxed and become healthy. Essential oils are extracted from aromatic plants to act as a medium which is then exposed to someone by massaging, bathing, perfuming and so on. This method has existed since the ancient times of Egypt and is now gaining a lot of attention in Europe. A French scientist named René Maurice Gattefossé published his research results on aromatherapy in a scientific journal, which sparked interest in many people. His research found that the plant's essential oils can reach deep layer tissues of skin, which is then absorbed by blood vessels and to reach organs that need to be treated by blood circulation.

Therefore, the present invention provides a gas generator for health use. The gas generator can produce health gas for health care that makes people feel relaxed and is also suitable for medical treatment.

SUMMARY OF THE INVENTION

One objective of the present invention is to provide an anti-explosion gas generator for health use. The anti-explosion gas generator for health use can generate a gas mixture of hydrogen and oxygen for being inhaled by a user.

Another objective of the present invention is to provide an anti-explosion gas generator for health use. The anti-explosion gas generator for health use can generate a gas mixture of hydrogen and oxygen, then mix the gas mixture with an atomized medicine, water vapor or a volatile essential oil for being inhaled by a user.

According to an embodiment of the present invention, the anti-explosion gas generator for health use comprises an electrolysis device and a gas mixing system. The electrolysis device is adapted for electrolyzing water to produce a gas mixture of hydrogen and oxygen. The gas mixing system is coupled to the electrolysis device to receive the gas mixture and to mix the gas mixture with water vapor, an atomized medicinal liquid, a volatile essential oil or a combination thereof, so as to produce a health gas for being inhaled by a user.

According to another embodiment of the present invention, the anti-explosion gas generator for health use further comprises a gas feeding element coupled between the electrolysis device and the gas mixing system. The gas feeding element is adapted for introducing a gas into the gas mixture of hydrogen and oxygen to reduce the concentration of hydrogen. Furthermore, in one of embodiments the added gas is air, an inert gas, water vapor or a combinations thereof.

According to another embodiment of the present invention, the anti-explosion gas generator for health use further comprises a flow controller coupled to the electrolysis device. The flow controller is adapted for controlling the quantity of the gas mixture flowing into the gas mixing system, thereby reducing the concentration of hydrogen in the gas mixture.

According to another embodiment of the present invention, the anti-explosion gas generator for health use further comprises a flow meter coupled to the electrolysis device. When the flow meter senses an abnormal level of the gas mixture generated from the electrolysis device (such as sensing a gas level greater or less than a predetermined safety value), the flow meter will cut off the power supplied to the electrolysis device, thereby reducing the concentration of hydrogen in the gas mixture.

According to another embodiment of the present invention, the gas mixing system further comprises a humidifier and an atomized/volatile gas mixing tank. The humidifier is coupled to the electrolysis device for receiving the gas mixture to generate a filtered gas. The atomized/volatile gas mixing tank is coupled to the humidifier for receiving the filtered gas and then mixing the filtered gas with an atomized gas to generate a health gas.

According to another embodiment of the present invention, the anti-explosion gas generator for health use further comprises a conversion valve coupled between the humidifier and the atomized/volatile gas mixing tank. The conversion valve is adapted to selectively connect the humidifier to the atomized/volatile gas mixing tank, so that the filtered gas can be mixed with the atomized gas to generate the health gas. Further, the conversion valve can selectively disconnect the humidifier from the atomized/volatile gas mixing tank, so that the filtered gas is output directly. The humidifier comprises a pure water tank for filtering the gas mixture of hydrogen and oxygen to generate the filtered gas. The atomized/volatile gas mixing tank comprises an oscillator for atomizing or vaporizing a liquid to produce the atomized gas. The liquid can be an essential oil, a medicinal liquid, pure water or a combination thereof. The atomized gas can be a volatile essential oil, an atomized medicine, water vapor or a combination thereof. Furthermore, the anti-explosion gas generator for health use is configured to selectively output the filtered gas or the health gas by turning on/off the oscillator.

According to another embodiment of the present invention, the humidifier further comprises a pressure sensor and a release valve. The pressure sensor is used for detecting whether the pressure of the filtered gas exceeds beyond a predetermined level. When the pressure is higher than the predetermined level, the pressure sensor is programmed to open the release valve to reduce the pressure of the filtered gas, thus achieving an explosion-proof effect.

The anti-explosion gas generator for health use according to the present invention can generate a gas mixture of hydrogen and oxygen, and the gas mixture can be selectively mixed with a volatile essential oil, an atomized medicine, water vapor or a combination thereof to form a health gas for being inhaled by a user. As the health gas includes a certain concentration of hydrogen, it provides anti-oxidation and an anti-aging effect. In addition, the atomized medicine in the health gas can be easily absorbed. Furthermore, the volatile essential oil in the health gas can relieve stress and improve the health of users.

Many other advantages and features of the present invention will be further understood by the following detailed description and the appended drawings.

BRIEF DESCRIPTION OF THE APPENDED DRAWINGS

To facilitate understanding, identical reference numerals have been used, where it is possible to designate identical elements that are common to the figures.

DETAILED DESCRIPTION OF THE INVENTION

In order to allow the advantages, spirit and features of the present invention to be more easily and clearly understood, the embodiments and appended drawings thereof are discussed in the following. However, the present invention is not limited to the embodiments and appended drawings.

Figure 1:
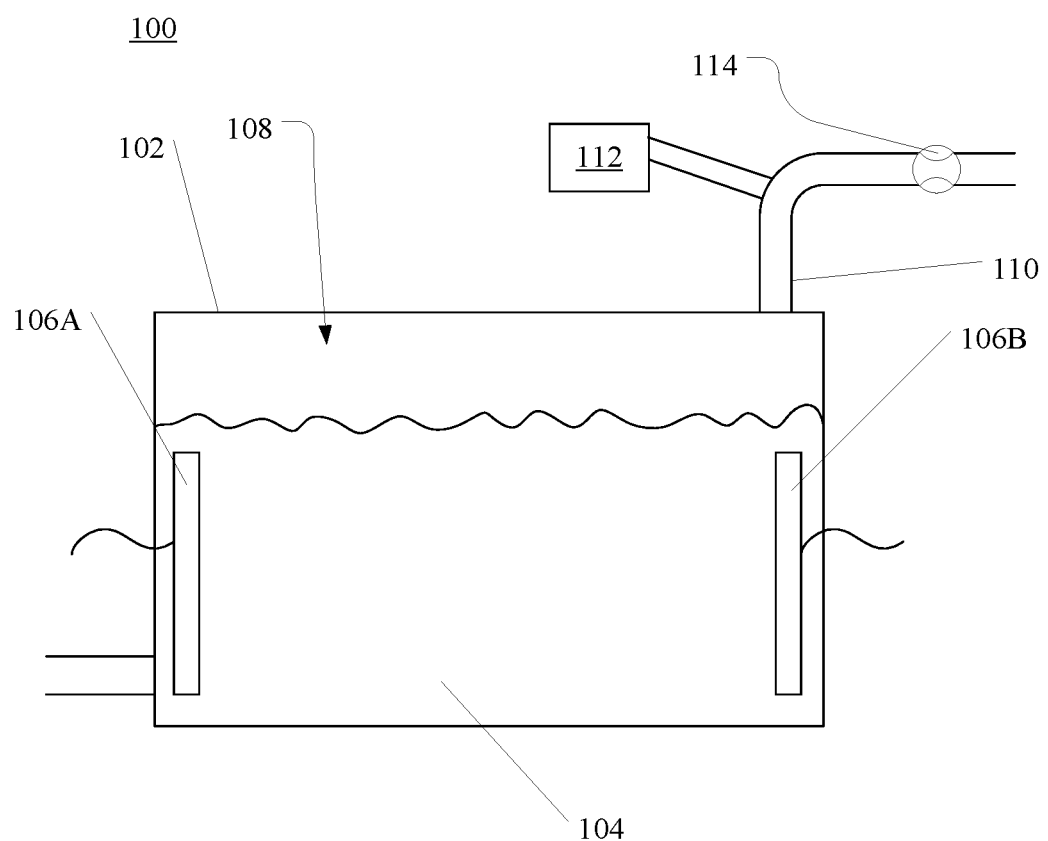
FIG. 1 is a schematic diagram illustrating an electrolysis device of an anti-explosion gas generator for health use according to an embodiment of the invention.

Please refer to FIG. 1. FIG. 1 is a schematic diagram illustrating an electrolysis device of an anti-explosion gas generator for health use according to an embodiment of the invention. The present invention provides an anti-explosion gas generator for health use which can generate a gas mixture of hydrogen and oxygen. In some embodiments, the gas mixture of hydrogen and oxygen is produced by the electrolysis of water. As shown in the figure, in some embodiments of the present invention, the electrolysis device 100 comprises an electrolysis tank 102 for accommodating electrolytic water 104. The main ingredients of the electrolytic water 104 is pure water, but electrolytes such as sodium hydroxide, calcium carbonate and sodium chloride can be added into the electrolyzed water 104 if necessary. The electrolysis tank 102 comprises two electrodes 106A and 106B, the two electrodes 106A and 106B respectively represent a cathode electrode and an anode electrode. The two electrodes 106A and 106B are coupled to a power supply (not shown) to provide the required power for the electrolysis device 100. In some embodiments, the polarity of the two electrodes 106A and 106B are fixed, for example, the electrode 106A is the cathode, the electrode 106B is the anode. In other embodiments, the polarity of the two electrodes 106A and 106B can be alternate, for example, at a point in time, the electrode 106A is the cathode and the electrode 106B is the anode, but after a predetermined time, the electrode 106A changes into the anode and the electrode 106B changes into the cathode.

After the two electrodes 106A and 106B are powered, the electrolyzed water 104 in the electrolysis tank 102 will start to be electrolyzed to generate hydrogen and oxygen. Hydrogen is formed on the cathode and oxygen is formed on the anode, and both hydrogen and oxygen are released to the upper part of the electrolysis tank 102 to form a gas mixture 108 of hydrogen and oxygen. The gas mixture 108 of hydrogen and oxygen is exported from a gas line 110 of the electrolysis tank 102 for usage. In another embodiment, hydrogen from the cathode and oxygen from the anode are exported and then mixed to form the gas mixture of hydrogen and oxygen. As the ratio of hydrogen to oxygen from the electrolysis of water is about 2:1 (H2: O2), the proportion of hydrogen in the combination gas may exceed 66%. In some embodiments, to prevent explosion of hydrogen, a gas feeding element 112 can be applied in the present invention to add a gas into the gas mixture 108, so as to reduce the concentration of hydrogen to an amount, for example, between 2% to 60%, such as an amount between 2% to 4%, wherein the gas can be air, water vapor, an inert gas (such as nitrogen), oxygen or combination thereof.

Reducing the flow rate of the gas mixture 108 can also have an explosion-proof effect. Therefore, in another embodiment, the gas line 110 comprises a flow controller 114 for controlling the flow rate of the gas mixture 108, so that the concentration of hydrogen in the gas mixture 108 can be reduced when the gas mixture 108 is transferred to a downstream device and mixed with the gas in the downstream device. In one embodiment, the flow controller 114 comprises a flow meter for detecting whether the flow rate of the gas mixture 108 from the electrolysis tank 102 is greater than a dangerous level (for example, the dangerous value should not exceed two liters per minute, i.e., 2 L/min, or 2000 c.c/min). The flow controller 114 can selectively shut down the power supplied to the electrolysis tank 102 to prevent excessive concentration of hydrogen. Sometimes the instability of the power supply will cause the concentration of hydrogen to be too high, thus, the gas line 110 and the electrolysis tank 102 can also be provided with the flow meter. However, if the concentration of hydrogen is too low, the health benefits of the present invention will be diminished. Therefore, the above dangerous level is preferably set to be no less than 0.1 L/min and more preferably between 0.1 L/min and 0.2 L/min. Of course, the flow meter (or the flow controller 114) can also be mounted at other locations as long as the flow rate of the gas mixture can be detected precisely. In other embodiments, the flow controller can comprise the flow meter and a computer (not shown), and the computer is stored with a pre-set parameter (such as reference table) representing the relationship between the power level (voltage×current) of the power supply and the flow rate of the gas mixture of hydrogen and oxygen. The computer is used for calculating parameter values every fixed time interval (for example, estimating the power level from the detected flow rate according to the reference table). If the flow rate of the gas mixture fails to correspond to the power level, it might indicate that the pressure of the gas mixture is too high and the flow controller would be activated to adjust the power supplied to the electrolysis tank 102, thereby reducing the produced amount of the gas mixture 108. That is to say, the flow controller 114 can selectively adjust the power level supplied to the electrolysis tank 102. Therefore, with the adjustment of the power level, the flow controller can control the flow rate of the gas mixture 108 to be between 0.1 L/min and 2 L/min and, more preferably, between 0.1 L/min and 0.2 L/min.

Figure 2:
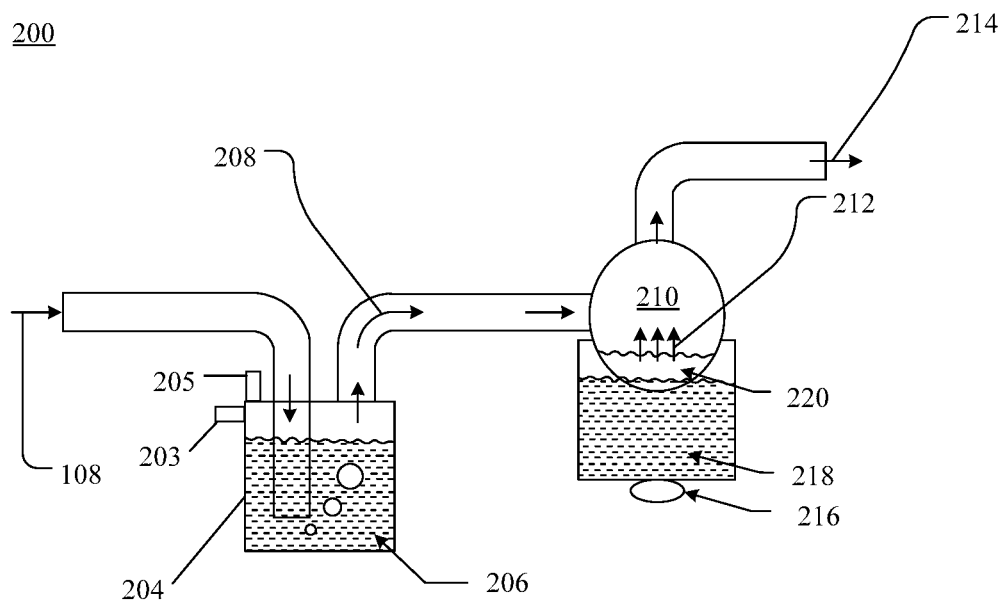
FIG. 2 is a schematic diagram illustrating a gas mixing system of an anti-explosion gas generator for health use according to an embodiment of the invention.

Please refer to FIG. 2. FIG. 2 is a schematic diagram illustrating a gas mixing system of an anti-explosion gas generator for health use according to an embodiment of the invention. The gas mixing system 200 is coupled to the electrolysis device 100 in FIG. 1, such as via the gas line 110 shown in FIG. 1, to receive the gas mixture 108. The gas mixing system 200 comprises a humidifier 204, such as a sink or a pure water tank, for filtering the gas mixture 108 with pure water 206, thereby generating the filtered gas 208. In some embodiments, the humidifier 204 is adapted to filter out other gases or impurities in the gas mixture 108 except hydrogen and oxygen, such as chlorine or a trace mount of metals. Therefore, the humidifier 204 is not limited to the pure water tank in this embodiment and can be any type of apparatus which is adapted to absorb gases other than hydrogen and oxygen. The gas mixing system 200 further comprises an atomized/volatile gas mixing tank 210 coupled to the humidifier 204 for receiving the filtered gas 208. The filtered gas 208 is then mixed with an atomized gas 212 to form a health gas 214. The atomized/volatile gas mixing tank 210 further comprises an oscillator 216 for atomizing or vaporizing a liquid 218 and a liquid 220 in the atomized/volatile gas mixing tank 210, thereby generating the atomized gas 212. The liquid 218 can be pure water to serve as an atomized base liquid. The liquid 220 can be an essential oil, a medicinal liquid, pure water or a combination thereof. The atomized gas 212 can be a volatile essential oil, an atomized medicine, water vapor or a combination thereof.

Furthermore, the anti-explosion gas generator for health use further comprises a pressure sensor 203 and a release valve 205 which is electrically connected to the pressure sensor 203. For example, as shown in FIG. 2, the pressure sensor 203 and the release valve 205 are coupled to the humidifier 204, wherein the pressure sensor 203 is used for detecting whether the pressure of the filtered gas is greater than a dangerous level (For example, 1 atm). If the pressure of the filtered gas is too high, the pressure sensor 203 would open the release valve 205 to reduce the pressure of the filtered gas, thus achieving an explosion-proof effect. In other words, the pressure sensor 203 can selectively open the release valve 205. Of course, the pressure sensor 203 and the release valve 205 can be coupled to other locations as long as the pressure sensor 203 and the release valve 205 can detect and reduce the pressure of the gas mixture. For example, the pressure sensor 203 and the release valve 205 can be coupled to the electrolysis device 100. By using the gas feeding element 112, the flow controller 114 (or the flow meter), the pressure sensor 203 and the release valve 205 in combination, the present invention can reduce the concentration of hydrogen and have an explosion-proof effect.

In other embodiments, the flow controller comprise the flow sensor and a computer (not shown), where the computer is stored with a pre-set parameter (such as a reference table) representing the relationship between the power level (voltage×current) of the power supply and the flow rate of the gas mixture of hydrogen and oxygen. The computer is adapted for calculating parameter values every fixed time interval (for example, estimating the power level from the detected flow rate according to the reference table). If the flow rate of the gas mixture fails to correspond to the power level, it might indicate that the pressure of the gas mixture is too high, and the computer would open the release valve 205 until the pressure reaches a preset safety value, and then close the release valve 205. However, if the release valve is opened too many times during a period of time (which can be cumulatively calculated by a counter) or there is a gas leakage problem, the computer can cut off the power of the electrolysis tank for security. That is to say, the computer can selectively open the release valve and cut off the power of the electrolysis tank.

Figure 3:
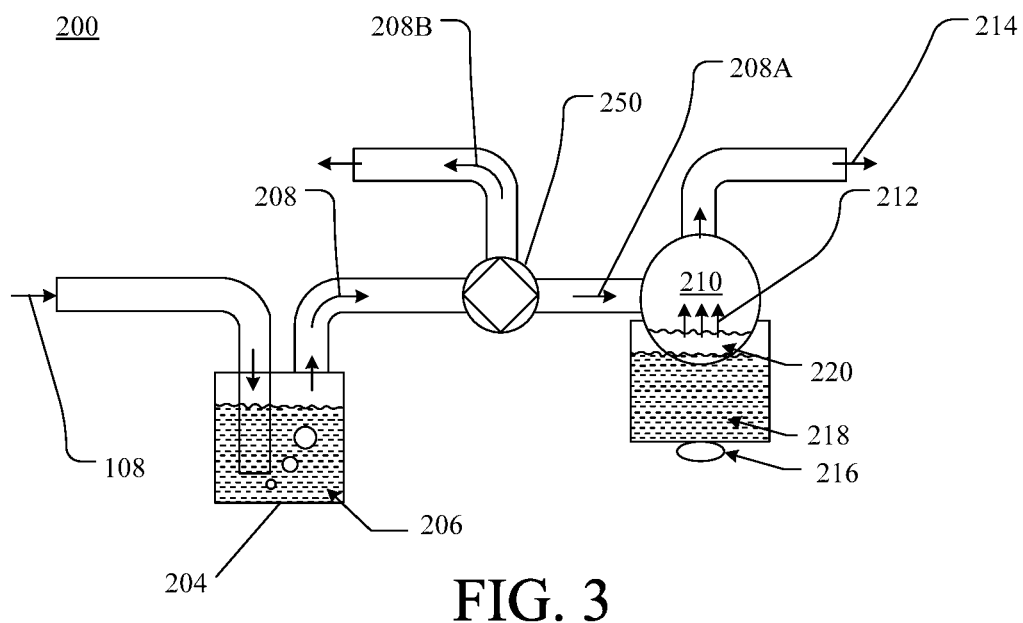
FIG. 3 is a schematic diagram illustrating a gas mixing system of an anti-explosion gas generator for health use according to another embodiment of the invention.

Please refer to FIG. 3. FIG. 3 is a schematic diagram illustrating a gas mixing system of an anti-explosion gas generator for health use according to another embodiment of the invention. In this embodiment, the anti-explosion gas generator for health use further comprises a conversion valve 250 coupled between the humidifier 204 and the atomized/volatile gas mixing tank 210, wherein the conversion valve 250 is adapted to selectively connect the humidifier 204 to the atomized/volatile gas mixing tank 210, so that the atomized gas 212 can be mixed with the filtered gas 208A to generate the health gas 214. The conversion valve is also adapted to selectively disconnect the humidifier from the atomized/volatile gas mixing tank, so that the filtered gas is directly output for being inhaled by a user. That is to say, the user has a choice in deciding whether the health gas should include the volatile essential oil, atomized medicine or water vapor or not by switching the conversion valve. This embodiment differs the embodiment of FIG. 2 in that this embodiment allows the user to breathe a gas mixture comprising only hydrogen and oxygen.

In another embodiment, a user can decide the composition of the health gas by other ways, such as by turning on/off the oscillator 216. For example, if the oscillator 216 is turned on, the filtered gas 208 will be mixed with the atomized gas 212 to generate the health gas 214; if the oscillator 216 is turned off, the filtered gas 208 will be exported directly for being inhaled by a user.

According to the above embodiments, the health gas 214 comprises hydrogen and oxygen, and optionally a volatile essential oil, an atomized medicine, water vapor or a combination thereof. Studies have found that there is an instable oxygen species (O+), also known as free radicals, in the human body. The free radicals are usually generated due to diseases, diet, environment and one's life style, and the free radicals in the human body can be excreted in the form of water by reacting with the inhaled hydrogen. With this method, the amount of free radicals in the human body can be reduced, thereby restoring the body condition from an acidic state to an alkaline state, achieving an anti-oxidation, anti-aging and beauty health effect, and even eliminating chronic diseases. In addition, according to the clinical studies, the atomized medicinal liquid is easier absorbed by the human body than its non-atomized counterpart. That is to say, compared with its non-atomized counterpart, the atomized medicine can achieve the same therapeutic effect with a much lower dosage amount. Furthermore, the drug's side effects can be reduced due to the low dosage amount of the atomized medicine administered. Therefore, the health gas 214 may lead to an excellent therapeutic effect. There are also clinical experiments showing that, for patients who need to inhale a high concentration of oxygen for a long time, the lung damage from the high concentration of oxygen can be ameliorated by inhaling hydrogen. Aside from those benefits, the volatile essential oil in the health gas can help general users improve their health and relieve stress.

With the examples and explanations mentioned above, the features and spirits of the invention are hopefully well described. Importantly, the present invention is not limited to the embodiments described herein. Those skilled in the art will readily observe that numerous modifications and alterations of the device may be made while retaining the teachings of the invention. Accordingly, the above disclosure should be construed as limited only by the metes and bounds of the appended claims.

What is claimed is:

1. An anti-explosion gas generator for health use, comprising:
   an electrolysis device configured for electrolyzing water to produce a gas comprising hydrogen, the electrolysis device comprising two electrodes and the electrodes having interchangeable polarity;
   a power supply electrically coupled to the electrolysis device and adapted for supplying power to the electrolysis device;
   a humidifier coupled to the electrolysis device and configured for receiving the gas comprising hydrogen to produce a filtered gas;
   an atomized/volatile gas mixing tank coupled to the humidifier and configured for receiving the filtered gas to selectively outputs either the filtered gas or a health gas, wherein the atomized/volatile gas mixing tank comprises an oscillator configured for vaporizing a liquid to produce a water vapor which is mixed with the filtered gas to generate the health gas, wherein the atomized/volatile gas mixing tank outputs the filtered gas when the oscillator is off and outputs the health gas when the oscillator is on; and
   a flow controller coupled to the electrolysis device and adapted for controlling a flow rate of the gas comprising hydrogen by adjusting a power level of the power supply supplied to the electrolysis device, wherein the flow rate of the gas comprising hydrogen is adjustable to change a concentration of hydrogen in the health gas.

2. The anti-explosion gas generator for health use of claim 1, further comprising a gas feeding element adapted for introducing a diluting gas to reduce the concentration of hydrogen in the health gas.

3. The anti-explosion gas generator for health use of claim 1, the flow controller comprising a reference table with a relationship between the power level of the power supply and the flow rate of the gas comprising hydrogen.

* * * * *